United States Patent
Gellert

(10) Patent No.: US 10,215,738 B2
(45) Date of Patent: Feb. 26, 2019

(54) MULTI-WAY VALVE

(71) Applicant: Siemens Aktiengesellschaft, Munich (DE)

(72) Inventor: Udo Gellert, Bellheim (DE)

(73) Assignee: Siemens Aktiengesellschaft, Munich (DE)

( * ) Notice: Subject to any disclaimer, the term of this patent is extended or adjusted under 35 U.S.C. 154(b) by 141 days.

(21) Appl. No.: 15/515,103

(22) PCT Filed: Sep. 23, 2015

(86) PCT No.: PCT/EP2015/071831
§ 371 (c)(1),
(2) Date: Mar. 28, 2017

(87) PCT Pub. No.: WO2016/050574
PCT Pub. Date: Apr. 7, 2016

(65) Prior Publication Data
US 2018/0231509 A1    Aug. 16, 2018

(30) Foreign Application Priority Data
Sep. 29, 2014  (DE) .................. 10 2014 219 712

(51) Int. Cl.
*F16K 7/00*    (2006.01)
*G01N 30/20*   (2006.01)
(Continued)

(52) U.S. Cl.
CPC ............ *G01N 30/20* (2013.01); *F16K 11/022* (2013.01); *G01N 2030/025* (2013.01);
(Continued)

(58) Field of Classification Search
CPC ..... Y10T 137/87716; Y10T 137/87764; Y10T 137/87249
(Continued)

(56) References Cited

U.S. PATENT DOCUMENTS 3,934,611 A * 1/1976 Gachot ............... F15C 3/04
137/884
4,688,602 A * 8/1987 Kitamura ........... B60H 1/0065
137/597

(Continued)

FOREIGN PATENT DOCUMENTS

| CN | 101986152 | 3/2011 |
| CN | 104048074 | 9/2014 |

*Primary Examiner* — R. K. Arundale
(74) *Attorney, Agent, or Firm* — Cozen O'Connor

(57) ABSTRACT

A multi-way valve has an upper part, a lower part and a central part connected to the upper part via an interposing first membrane and the lower part via an interposing second membrane, wherein the upper and lower parts contain recesses on the upper and lower part faces facing the membranes, where a control fluid is introducible into the recesses, the central part contains a pair of openings in regions opposite the recesses on the central part faces lying adjacent to the membranes, where while introducing the control fluid into a recess, the membrane closes respective opposite openings in the central part, and where the membrane otherwise recedes into the recess, thereby releasing the opposite openings, where valve connections are mounted on the upper or lower part such that the central part can have a very thin design while preventing dead regions in the channel systems.

11 Claims, 3 Drawing Sheets

(51) Int. Cl.
*F16K 11/02* (2006.01)
*G01N 30/02* (2006.01)

(52) U.S. Cl.
CPC . *G01N 2030/201* (2013.01); *G01N 2030/204* (2013.01); *Y10T 137/87716* (2015.04); *Y10T 137/87764* (2015.04)

(58) Field of Classification Search
USPC .......................................................... 73/23.42
See application file for complete search history.

(56) References Cited

U.S. PATENT DOCUMENTS

| | | | |
|---|---|---|---|
| 5,203,368 A | | 4/1993 | Barstow et al. |
| 5,496,009 A | | 3/1996 | Farrell et al. |
| 5,775,371 A | * | 7/1998 | Pan .......................... F15C 3/04 |
| | | | 137/597 |
| 6,453,725 B1 | | 9/2002 | Dahlgren et al. |
| 6,601,606 B2 | * | 8/2003 | Xu ........................ F16K 11/022 |
| | | | 137/341 |
| 2003/0233863 A1 | * | 12/2003 | Cordill ................... G01N 30/20 |
| | | | 73/23.42 |
| 2014/0260538 A1 | | 9/2014 | Pratt et al. |

* cited by examiner

MULTI-WAY VALVE

CROSS-REFERENCE TO RELATED APPLICATIONS

This is a U.S. national stage of application No. PCT/EP2015/071831 filed 23 Sep. 2015. Priority is claimed on German Application No. 10 2014 219 712.0 filed 29 Sep. 2014, the content of which is incorporated herein by reference in its entirety.

BACKGROUND OF THE INVENTION

1. Field of the Invention

The invention relates to a multi-way valve having at least three valve connections, of which at least one pair of adjacent valve connections is connected fluidically in a first valve position and is separated fluidically in a second valve position and at least one further pair of adjacent valve connections is separated fluidically in the first valve position and connected fluidically in the second valve position, and an upper part, a lower part and a plate-shaped central part, which is connected to the upper part with the interposition of a first membrane and to the lower part with the interposition of a second membrane.

2. Description of the Related Art

U.S. Pat. No. 6,453,725 B1 disclose a conventional multi-way valve.

U.S. Pat. No. 5,203,368 A discloses an individual valve having a plate-shaped upper part, a lower part and a central part, between which and the lower part a membrane is disposed. The lower part contains a recess which is opposite to two openings in the central part. Depending on whether an overpressure or vacuum is generated in the recess using a control fluid, the membrane closes or releases the openings. The openings are connected via passages with grooves on the side of the central part facing away from the membrane. The grooves covered by the overlying upper part form laterally extending fluid channels, which lead to valve connections.

U.S. Pat. No. 5,496,009 A discloses a multi-way valve in the form of a valve matrix with at least four valves, in order to connect at least two inflow channels individually with at least two outflow channels. The multi-way valve has a plate-shaped upper part, a lower part and a central part, where a membrane is disposed between the upper part and the central part and a sealing film is disposed between the lower part and the central part. The inflow channels are formed by parallel grooves on the upper side of the central part, which are covered by the membrane. The outflow channels are formed by parallel grooves extending horizontally thereto on the lower side of the central part, which are covered by the sealing film. The upper part contains a recess for each valve in each case, where the recess, in the central part, is opposite to one of the inflow channels and an opening connected with one of the outflow channels. Depending on whether an overpressure or vacuum is generated in the recess using a control fluid, the membrane closes or releases the opening and the inflow channel.

The multi-way valve known from the afore-cited U.S. Pat. No. 6,453,725 B1 can be used for sample dosing and separation column switchover in gas chromatography. Here, for instance, in a first valve position, a sample taken from a technical process is routed in a continuous stream through a dosing loop with a defined dosing volume, for instance. At the same time, a separation device of the gas-phase chromatograph consisting of a separation column or a number of connected separation columns is purged with a carrier gas. In a second valve position, the sample quantity contained in the dosing loop is guided through the separation device via the carrier gas, broken down into different sample components and then detected, while the sample flow is routed past the dosing loop.

One example of a conventional multi-way valve is shown cross-sectionally in FIG. 1, in FIG. 2 in a longitudinal section along line AA', in FIG. 3 in a schematically convoluted section along circular line BB' in a first valve position, and in FIG. 4 in a second valve position.

The multi-way valve consists of a cylindrical upper part 1, a cylindrical lower part 2 and a central part 3, in the form of a cylindrical plate, which is connected with the upper part 1 with the interposition of a first membrane 4 and with the lower part 2 with the interposition of a second membrane 5. Ten valve connections 6a-6j are mounted on the central part 3 in the circumferential direction and at the same angular distance from one another, by way of which valve connections fluids that are to be switched or distributed to the valve are supplied or are guided out of the valve. For each valve connection 6a-6j, in each case the central part 3 contains a channel system, e.g., 7i, with a first opening 8i on the upper side of the central part 3, a second opening 9i on the lower side of the central part 3 and a third opening 10i for connection with the valve connection 6i. In the example shown, the channel system 7i consists of a channel section connecting the openings 8i and 9i on the upper side and lower side of the central part 3 in the quickest way with one another and a channel section branching therefrom centrally in a T-shape in the direction toward the valve connection 6i.

With the conventional multi-way valve shown by way of example, there is provision for the adjacent valve connections 6a and 6b, 6c and 6d, 6e and 6f, 6g and 6h and 6i and 6j which each form a pair to be connected fluidically with one another in the first valve position shown in FIG. 3 and to be separated fluidically in the second valve position shown in FIG. 4. Further pairs of adjacent valve connections 6b and 6c, 6d and 6e, 6h and 6i, and 6j and 6a are conversely separated fluidically in the first valve position and connected fluidically in the second valve position.

The fluidic connection or separation of the various pairs of adjacent valve connections is performed with the aid of the two membranes 4 and 5, by these alternately being applied with pressure or relieved of pressure on their side facing away from the central part 3. To this end, on its side facing the first membrane 4, the upper part 1 contains a recess 11 for each pair of adjacent valve connections, e.g., 6a and 6b to be connected fluidically in the first valve position, which recess is opposite to the first openings 8a, 8b assigned to the relevant pair on the upper side of the central part 3.

With the pairs of adjacent valve connections, e.g., 6b and 6c, which are to remain separated in the first valve position, there is no shared recess in the upper part 1 that is opposite to the assigned first openings 8b, 8c, so that at this location the membrane 4 is pressed by the upper part 1 directly against the central part 3 and thus separates the first openings 8b, 8c from one another. All recesses 11 are connected by way of channels 12 to a first control fluid connection 13, by way of which the first membrane 4 can be loaded or unloaded with a control fluid 14 (pressurized air) which can be activated or deactivated.

The lower part 2 similarly contains a recess 15 on its side facing the second membrane 5 for each pair of adjacent valve connections, e.g., 6b and 6c, to be connected fluidically in the second valve position, where the recess is opposite to the second openings 9b, 9c assigned to the relevant pair on the lower side of the central part 3. With the pairs of adjacent valve connections, e.g., 6a, 6b or 6f, 6g that are to remain separated in the first valve position, there is no shared recess in the lower part 2 that is opposite to the assigned second openings 9a, 9b or 9f, 9g so that at this location the second membrane 5 is pressed by the lower part 2 directly against the central part 3 and thus separates the second openings 9a, 9b or 9f, 9g from one another. All recesses 15 are connected by way of channels 16 with a second control fluid connection 17, by way of which the second membrane 5 is loaded or unloaded with the control fluid 14 which can be activated or deactivated.

In the first valve position shown in FIG. 3, the second membrane 5 is loaded with the control fluid 14, while the first membrane 4 is unloaded. The second membrane 5 therefore joins to the central part 3 and closes the second openings 9a-9j. In contrast, the unloaded first membrane 4 eases the pressure of the fluid supplied to the valve via individual valve connections 6a-6j and recedes into the recesses 11, so that the second first openings, e.g., 8a and 8b, are released and the assigned valve connections 6a, 6b are connected fluidically with one another.

In the second valve position shown in FIG. 4, the first membrane 4 is loaded with the control fluid 14, while the second membrane 5 is unloaded. The first membrane 4 therefore joins to the central part 3 and closes the first openings 8a-8j. In contrast, the unloaded second membrane 5 eases the pressure of the fluid supplied to the valve and recedes into the recesses 15 so that the opposing second openings, e.g., 8b and 8c, are released and the assigned valve connections 6b, 6c are connected fluidically to one another.

On account of the dead volumes of the conventional multi-way valve, its use can be restricted in certain applications. For instance, the valve connection 6b in the first valve position is supplied with a first fluid by way of the valve connection 6a and in the second valve position is supplied with a second fluid via the valve connection 6c. During or immediately after switchover from the first into the second valve position, a part of the channel system 7b, i.e., the dead space of the now closed first opening 8b up to the center of the channel section disposed between the openings 8b and 9b, is filled with the first fluid, which then diffuses into the second fluid with a delay. With the example from the gas chromatography mentioned in the introduction, the first fluid can be the sample that is routed through the dosing loop during the first valve position and in the second valve position is transferred via the carrier gas out of the dosing loop into the chromatographic separation device. The diffusion of the sample from the dead volume into the carrier gas results in an imprecise injection of the sample into the flow of carrier gas, which results in a reduction in the resolution of the subsequent chromatographic separation (peak with shoulders).

SUMMARY OF THE INVENTION

In view of the foregoing, it is an object of the invention to reduce the dead volumes of a conventional multi-way valve.

This and other object and advantages are achieved in accordance with the invention by a multi-way valve in which, for each valve connection in each case the central part contains a channel system with a first opening on the upper side of the central part, a second opening on the lower side of the central part and a third opening for connection with the valve connection, where on its side facing the first membrane, the upper part contains a recess for each pair of adjacent valve connections connected fluidically in the first valve position in each case, where the recess is opposite to the first openings assigned to the pair on the upper side of the central part such that, upon deflection into the recess, the first membrane releases the first openings and closes the first openings when pressure is applied with a control fluid in the recess and, on its side facing the lower membrane, the lower part contains a recess for each further pair of adjacent valve connections connected fluidically in the second valve position in each case, where the recess is opposite to the second openings assigned to the further pair on the lower side of the central part such that, upon deflection into the recess, the second membrane releases the second openings and closes the second openings when pressure is applied with the control fluid in the recess.

In accordance with the invention, the valve connections are mounted on the upper part and/or the lower part, the third openings contained in the central part for connection with the valve connections lie on the upper side or lower side of the central part, the first or second membrane with the third openings contains aligned passages, and the upper part or lower part contains channels for the fluidic connection of the valve connections with the passages.

With a conventional multi-way valve, the dead volumes are determined by the thickness or installation height of the central part, which is in turn dependent on the installation or assembly dimensions of the valve connections. By the valve connections being transferred from the central part into the upper part or lower part, the thickness of the central part and thus the dead volumes can be reduced almost arbitrarily. The valve connections can be mounted together either in just the upper part or in just the lower part, or they can, preferably with respect to the same parts, be distributed on the upper and lower part, in order to use the assembly space available on the valve optimally and if necessary to minimize the installation volume of the valve. The valve connections can also be mounted radially and/or axially on the upper and lower part.

The channel system assigned in each case to each valve connection in the central part contains the first opening on its upper side, the second opening on the lower side and the third opening on the upper or lower side. Here, the first and second opening are, like already with the conventional multi-way valve, preferably connected in the shortest way with one another by way of a straight connecting channel. A further L-shaped channel can branch from this connecting channel to the third opening. In order to realize the L-shaped channel, the central part is preferably made up of two plates, where grooves are formed in one or both plates, such as by etching, which after assembling the plates, if necessary by interposing a sealing film, form the part of the L-shaped channel that extends in parallel to the upper or lower side of the central part.

The use of the inventive multi-way valve in a gas-phase chromatograph permits an essentially more precise sample dosing, which in turn makes shorter chromatography cycles possible without other separation columns being required. Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

To further explain the invention, reference is made below to the figures of the drawing, in which.

DETAILED DESCRIPTION OF THE EXEMPLARY EMBODIMENTS

The example of the conventional multi-way valve shown in FIGS. 1 to 4 was already described above.

Figure 1:
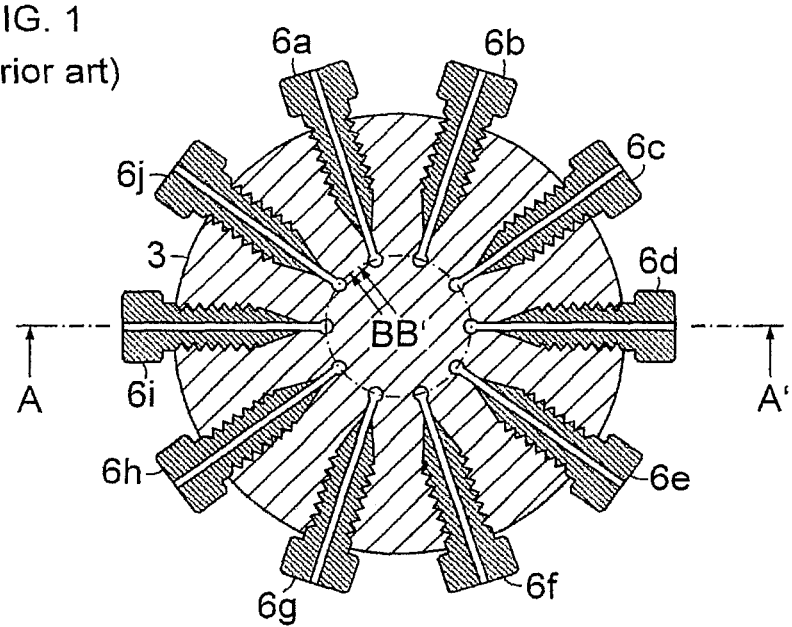
FIG. 1 shows an exemplary cross-sectional view of a conventional multi-way valve.
Figure 2:
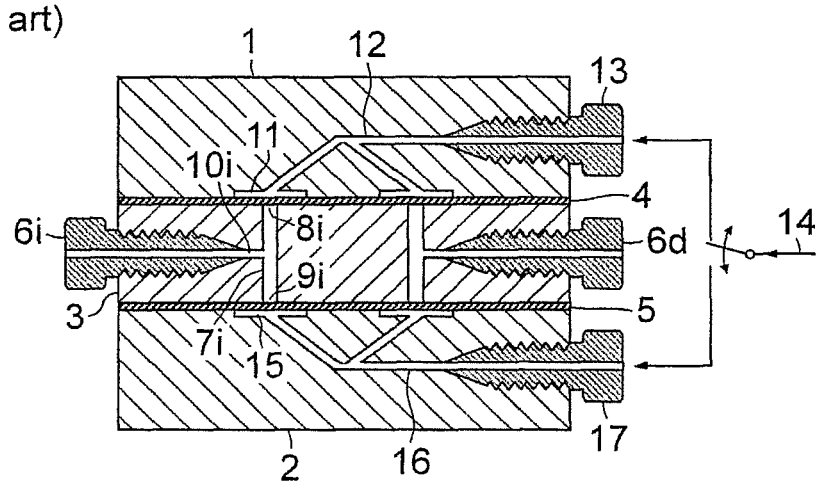
FIG. 2 shows the multi-way valve of FIG. 1 in a longitudinal section along line AA'.
Figure 3:
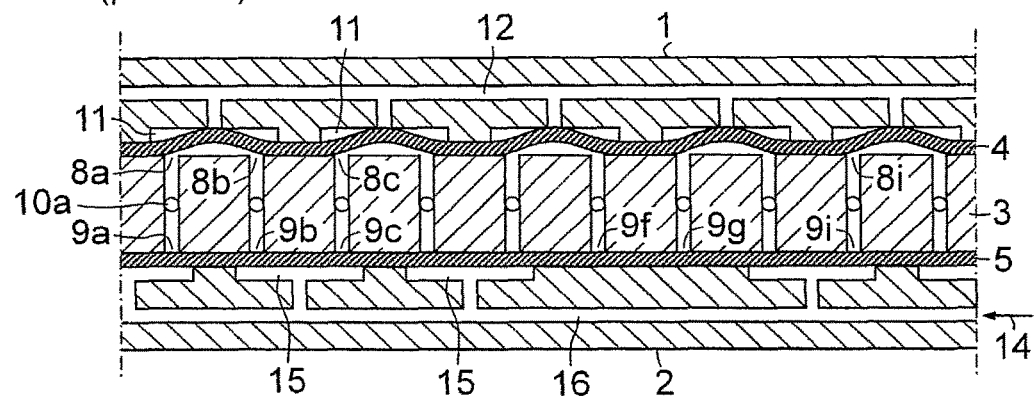
FIG. 3 shows the multi-way valve of FIG. 1 in a schematically convoluted section along the circular line BB' in a first valve position.
Figure 4:
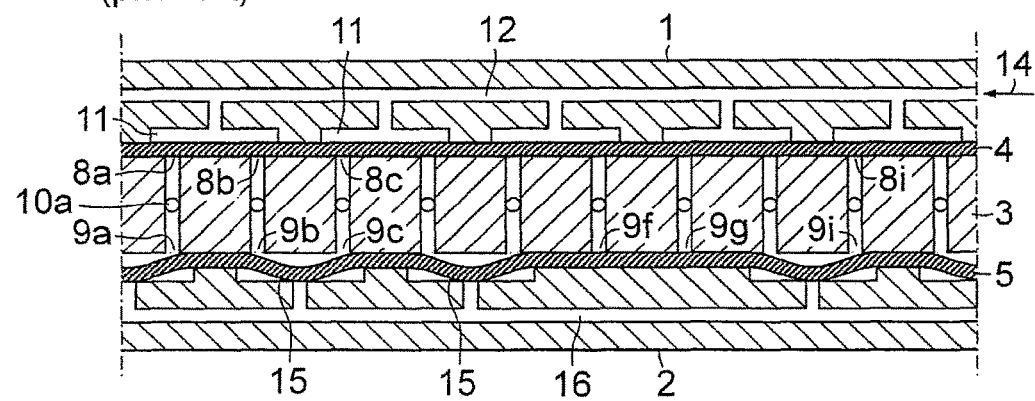
FIG. 4 shows the multi-way valve of FIG. 1 in a schematically convoluted section along the circular line BB' in a second valve position.
Figure 5:
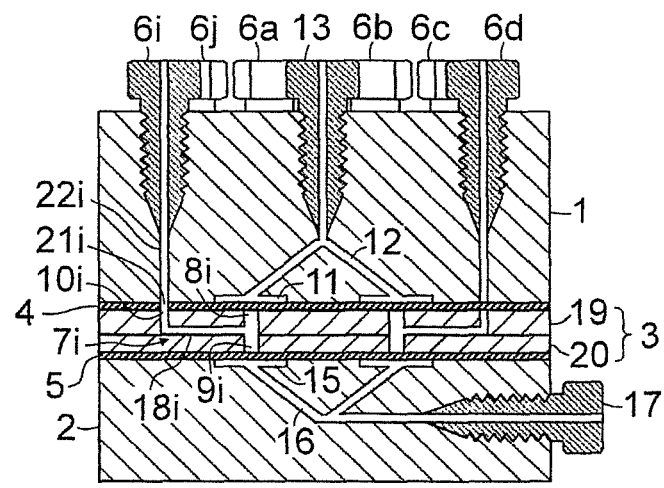
FIG. 5 shows a cross-section of an exemplary multi-way valve in accordance with an embodiment of the invention.

FIG. 5 shows a cross-section through a first exemplary embodiment of the inventive multi-way valve. The known valve also consists of an upper part 1, a lower part 2 and a central part 3, which is connected with the upper part 1 with the interposition of a first membrane 4 and with the lower part 2 with the interposition of a second membrane 5. Contrary to the conventional multi-way valve, the ten valve connections 6a-6j, of which only connections 6a-6d, 6i and 6j can be seen here, are mounted on the upper part 1 in the axial direction. The central part 3 contains a channel system for each valve connection 6a-6j, e.g., the channel system 7i described below as representative of the other channel systems, having a first opening 8i on the upper side of the central part 3, a second opening 9i on the lower side of the central part 3 and a third opening 10i on the upper side of the central part 3 for connection with the valve connection 6i. In the example shown, the channel system 7i consists of a connecting channel connecting the openings 8i and 9i on the upper and lower side of the central part 3 in the shortest way with one another and a channel 18i branching away therefrom centrally in a T-shape and extending in an L-shape toward the third opening 10i. To realize the L-shaped channel 18i, the central part 3 is made up of two plates 19, 20, where grooves are formed in the plate 19 by a micromechanical method, such as etching, which, after assembling the plates 19, 20, form the part of the L-shaped channel 18i that extends parallel to the upper or lower side of the central part 3. The part of the channel 18i that extends axially to the third opening 10i is likewise manufactured micromechanically. Passages 21i aligned with the third openings, e.g., 10i, are stamped into the first membrane 4, from which further channels 22i in the upper part 3 lead to the valve connections 6i.

In the same manner as the conventional multi-way valve, on its side facing the first membrane 4, the upper part 1 contains a recess 11 in each case for each pair of adjacent valve connections to be connected fluidically in the first valve position, which recess is opposite to the first openings (here, e.g., the opening 8i of the pair 8i, 8j) assigned to the relevant pair on the upper side of the central part 3. All recesses 11 are connected with a first control fluid connection 13 by way of channels 12, where the control fluid connection is mounted axially here in the center of the upper part and by way of which the first membrane 4 can be loaded or unloaded with a control fluid which can be activated or deactivated.

The lower part 2 similarly contains a recess 15 on its side facing the second membrane 5, for each pair of adjacent valve connections to be connected fluidically in the second valve position, where the recess is opposite to the second openings (here, e.g., the opening 9i of pair 9i, 9j) assigned to the relevant pair on the lower side of the central part 3. All recesses 15 are connected by way of channels 16 with a second control fluid connection 17, by way of which the second membrane 5 can be loaded or unloaded with a control fluid that can be activated or deactivated.

The representation of the multi-way valve is very simplified and in particular not shown true to scale. The central part 3 thus comprises an installation height in the order of magnitude of a millimeter and less, which is first enabled by positioning the valve connections 6a-6j in the upper part 1. Accordingly, the dead spaces of the connecting channel between the first opening 8i and the second opening 9i are minimal.

Figure 6:
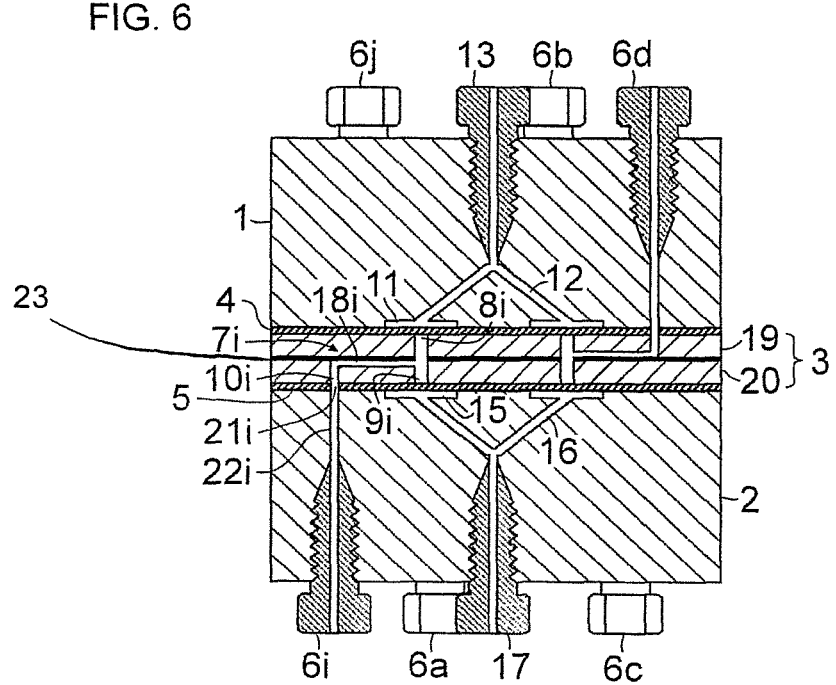
FIG. 6 shows a further exemplary embodiment of the multi-way valve in accordance with the invention.

The further exemplary embodiment of the inventive multi-way valve shown in FIG. 6 differs from that in FIG. 5 in that the valve connections 6b, 6d, 6f, 6h, 6j are mounted on the upper part 1 and the other valve connections 6a, 6c, 6e, 6g, 6i are mounted on the lower part 2. The two plates 19, 20 of the central part 3 are assembled with the interposition of a sealing film 23.

The described multi-way valve with its ten valve connections 6a-6j can be used for sample dosing (injection) and separation column switchover in a gas-phase chromatograph. Six valve connections are sufficient for the exclusive use for sample dosing. A further advantageous use with the two-dimensional gas chromatography is the dosing of the eluate of a first separation column in a second separation column, where a very high dosing quality is demanded.

Thus, while there have been shown, described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those element steps which perform substantially the same function in substantially the same way to achieve the same results are within the scope of the invention. Moreover, it should be recognized that structures and/or elements shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A multi-way valve comprising:
   at least three valve connections, at least one pair of adjacent valve connections being connected fluidically in a first valve position and being separated fluidically in a second valve position, and at least one further pair of adjacent valve connections being separated fluidically in the first valve position and being connected fluidically in the second valve position;

an upper part;

a lower part; and a plate-shaped central part connected to the upper part via an interposing first membrane and connected to the lower part with the interposition of a second membrane;

wherein, for each valve connection, the central part includes a channel system having a first opening on an upper side of the central part, includes a second opening on a lower side of the central part and includes a third opening for connection with a first valve connection of the at least three valve connections;

wherein the upper part, on its side facing the first membrane, includes a recess for each pair of adjacent valve connections connected fluidically in the first valve position in each case, said recess being opposite to first openings assigned to the pair of adjacent valve connections on the upper side of the central part, such that upon deflection into the recess, the first membrane releases the first openings and closes the first openings when pressure is applied with a control fluid in the recess;

wherein the lower part, on its side facing the lower membrane, includes a recess for each further pair of adjacent valve connections connected fluidically in the second valve position, said recess being opposite to openings assigned to the further pair on the lower side of the central part such that, upon deflection into the recess, the second membrane releases the second openings and closes the second openings when pressure is applied with the control fluid in the recess;

wherein the at least three valve connections are mounted on at least one of (i) the upper part and (ii) the lower part;

wherein the third openings, for connection with the first valve connection of the at least three valve connections, contained in the central part lie on the upper side or lower side of the central part;

wherein the first or second membrane with the third openings contains aligned passages; and wherein the upper part or lower part contains channels for fluidic connection of the valve connections with the passages.

2. The multi-way valve as claimed in claim 1, wherein one part of the at least three valve connections is mounted on the upper part and a remaining part is mounted on the lower part.

3. The multi-way valve as claimed in claim 1, wherein half of the at least three valve connections is mounted on the upper part and a remaining part is mounted on the lower part.

4. The multi-way valve as claimed in claim 1, wherein the central part consists of two assembled plates, wherein grooves are formed in at least one of the two assembled plates which, after assembling the plates, form parts of the channel system which extend in parallel to the upper or lower side of the central part.

5. The multi-way valve as claimed in claim 4, wherein the plates are assembled with an interposing sealing film arranged between the plates.

6. The multi-way valve as claimed in claim 1, wherein the central part has an installation height in an order of magnitude of a millimeter.

7. The multi-way valve as claimed in claim 1, wherein the multi-way valve is implemented within a gas-phase chromatograph.

8. The multi-way valve as claimed in claim 7, wherein sample dosing with the multi-way valve is performed in the gas-phase chromatograph.

9. The multi-way valve as claimed in claim 7, wherein separation column switchover is implemented via the multi-way valve in the gas-phase chromatograph.

10. The multi-way valve as claimed in claim 8, wherein separation column switchover is implemented via the multi-way valve in the gas-phase chromatograph.

11. The multi-way valve as claimed in claim 7, wherein the multi-way valve is implemented to perform dosing of an eluate of a first separation column in a second separation column of the gas-phase chromatograph.

* * * * *